(12) United States Patent
Winter

(10) Patent No.: US 7,115,552 B2
(45) Date of Patent: Oct. 3, 2006

(54) SPIROEPOXY-MACROCYCLE AS PERFUMING INGREDIENT

(75) Inventor: Beat Winter, Bernex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/369,319

(22) Filed: Mar. 6, 2006

(65) Prior Publication Data

US 2006/0148673 A1    Jul. 6, 2006

Related U.S. Application Data

(63) Continuation of application No. PCT/IB04/003154, filed on Sep. 24, 2004.

(30) Foreign Application Priority Data

Oct. 23, 2003  (WO) .................. PCT/IB03/04726

(51) Int. Cl.
*C11B 9/00* (2006.01)
(52) U.S. Cl. ................... 512/9; 512/8; 512/14; 512/25
(58) Field of Classification Search .................. 512/8, 512/9, 14, 25
See application file for complete search history.

(56) References Cited

FOREIGN PATENT DOCUMENTS

| EP | 0384034 | 8/1990 |
|---|---|---|
| FR | 2 252 840 | 6/1975 |
| GB | 1 494 915 | 12/1977 |

OTHER PUBLICATIONS

Matthias Nagel et al., XP-001204436, "Short and Versatile Two-Carbon Ring Expansion Reactions by Thermosomerization: Novel Straightforward Synthesis o (±)-Muscone, Nor-and Homomuscones, and Further Macrocyciic Ketones" Synlett, No. 2, pp. 280-284 (2002), no month.
David M- Hodgson, XP-0 0 2 3 1 0 9 7 0 "Straightforward synthesis of α-β-epoxysilanes from terminal epoxides by lithium 2,2,6,6-tetramethylpiperidide-mediated deprotonation-in situ silylation" Tetrahedron Letters, vol. 43, pp. 7895-7897(2002), no month.
Miao Wang et al., Acrylates / Hydroxyesters Acrylates Copolymer in Personal Care .Applications: AcudyneTM DHR Durable Hold Resin, Rohm and Haas Company, no date.

*Primary Examiner*—Monique T. Cole
(74) *Attorney, Agent, or Firm*—Winston & Strawn LLP

(57) ABSTRACT

The present invention relates to the use as perfuming ingredient of 1-oxaspiro[2.11]tetradecane, as well as to the perfuming compositions or perfumed articles containing said compound.

4 Claims, No Drawings

SPIROEPOXY-MACROCYCLE AS PERFUMING INGREDIENT

CROSS-REFERENCE TO RELATED APPLICATIONS

This application is a continuation of International application PCT/IB2004/003154 filed Sep. 24, 2004, the entire content of which is expressly incorporated herein by reference thereto.

TECHNICAL FIELD

The present invention relates to the field of perfumery. More particularly, it concerns the use as perfuming ingredient of 1-oxaspiro[2.11]tetradecane.

BACKGROUND

1-Oxaspiro[2.11]tetradecane is a known chemical, which has been described in several prior art documents as chemical intermediate in various chemical transformations, for example see Nagel et al. in Synlett, 2002, 280.

However, to the best of our knowledge, none of the prior art documents report or suggest any organoleptic properties, or use in the field of perfumery, of said compound.

SUMMARY OF THE INVENTION

The invention relates about the use of 1-oxaspiro[2.11]tetradecane as perfuming ingredient as well as the perfuming compositions or perfumed articles containing said compound.

DETAILED DESCRIPTION OF THE PREFERRED EMBODIMENT

We have now surprisingly discovered that 1-oxaspiro[2.11]tetradecane of formula

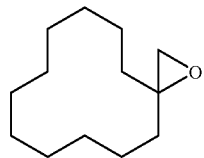

(I)

is a useful perfuming ingredient which can be used in several fields of the modern perfumery, to impart odor notes of the woody type.

The invention's compound possesses a woody, camphoraceous odor with ambry and earthy-Vetyver aspects. The odor of the invention's compound is in some way reminiscent of the one of Cashmeran® (6,7-dihydro-1,1,2,3,3-pentamethyl-4(5H)-indanone, origin: IFF).

The odor properties of 1-oxaspiro[2.11]tetradecane have proved to be very useful in the field of fine perfumery. Indeed, the invention's compound can be advantageously added into fine perfumery bases to impart a warm and sheer woody character, which is also powerful and diffusive. The overall effect imparted by the addition of the invention's compound has also been considered, by a panel of perfumers, as being more balanced and elegant than the one which could be conferred by the addition of other prior art compounds, such as CASHMERAN®, known to impart similar odor notes.

Furthermore, compound (I) can also be advantageously added into perfuming base for functional perfumery, where it is able to confer a well perceivable woody character, in particular to the fragrance's top-notes.

Therefore, in view of the surprising properties of 1-oxaspiro[2.11]tetradecane, the present invention concerns the use of the compound of formula (I) as perfuming ingredient. In other words it concerns a method to confer, enhance, improve or modify the odor properties of a perfuming composition or of a perfumed article, which method comprises adding to said composition or article an effective amount of the compound of formula (I). By "use of the compound of formula (I)" it has to be understood here also the use of any composition containing compound (I) and which can be advantageously employed in perfumery industry as active ingredients.

These compositions, which in fact can be advantageously employed as perfuming ingredient, are also an embodiment of the present invention.

Therefore, another embodiment of the present invention is a perfuming composition comprising:

i) as perfuming ingredient, the invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e., that does not significantly alter the organoleptic properties of perfuming ingredients. This carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for examples, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996.

Generally speaking, by "perfumery base" we mean here a composition comprising at least one perfuming co-ingredient.

By "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery adjuvant" we mean here an ingredient capable of imparting additional added benefit such as a color, a particular light resistance, chemical stability and etc. A detailed description of the nature and type of adjuvant commonly used in perfuming bases cannot be exhaustive, but it has to be mentioned that said ingredients are well known to a person skilled in the art.

An inventive composition that includes the compound of formula (I) and at least one perfumery carrier represents a particular embodiment of the invention as well as a perfuming composition comprising the compound of formula (I), at least one perfumery carrier, at least one perfumery base, and optionally at least one perfumery adjuvant.

Its is also understood here that any mixture resulting directly from a chemical synthesis, e.g., without an adequate purification, in which the compound of the invention would be involved as a starting, intermediate or end-product could not be considered as a perfuming composition according to the invention.

Therefore the mixture of compounds obtained as final product by Nagel et al. in Synlett, 2002, 280, and containing the invention's compound are specifically excluded. These excluded mixtures are:

A) a mixture containing 50–60% by weight of ciclotridecanone, about 25–35% of 1-oxaspiro[2.11]tetradecane and 5–10% of cyclodocedacone; and B) a mixture consisting of 90–95% of 1-oxaspiro[2.11] tetradecane and 5–10% of cyclodocedacone, percentage being relative to the total weight of the mixture.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, the compound of formula (I) or an invention's composition; and ii) a consumer product base;

is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired olfactif effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 40% by weight, or even more, of the compounds of the invention based on the weight of the composition into which they are incorporated. Concentrations lower than these, such as in the order of 0.1% to 15% by weight, can be used when these compounds are incorporated into perfumed articles, percentage being relative to the weight of the article.

As mentioned above, the compound of the invention is already known in the prior art, therefore its preparation does not need to be disclosed in further detail. However, as simple method of synthesis, one can cite a reaction of the Corey-Chaykovsky using cyclododecanone as starting material.

EXAMPLES

The invention will now be described in further detail by way of the following examples.

Example 1

Preparation of a Perfuming Composition

An alcoholic perfuming composition was prepared by admixing the following ingredients:

| Ingredient | Parts by weight |
| --- | --- |
| Benzyl acetate | 250 |
| Geranyl acetate | 600 |
| 10%* Methylnonylaldehyde | 25 |
| 10%* AMBROX ®[1)] | 25 |
| Bergamot abergapt | 750 |
| Caryophyllene | 25 |
| Lemon oil california | 300 |
| Citronellol | 450 |
| 10%* Damascenone[2)] | 100 |
| Dihydromyrcenol | 1000 |
| Eugenol | 50 |
| 10%* 7-Methyl-2H,4H-1,5-benzodioxepin-3-one | 150 |
| 3-(4-Methoxyphenyl)-2-methylpropanal | 125 |
| Galbanum essential oil | 75 |
| IRALIA ®[3)] | 300 |
| ISO E SUPER ®[4)] | 1000 |
| 10%* Isooctadienone | 10 |
| LILIAL ®[5)] | 400 |
| LYRAL ®[6)] | 800 |
| Mandarin essential oil | 400 |
| Muscenone[7)] | 300 |
| HEDIONE ®[5)] | 750 |
| Phenylethyl alcohol | 300 |
| ROMANDOLIDE ®[5)] | 750 |
| 3-(5,5,6-Trimethyl-bicyclo[2.2.1]hept-2-yl)-1-cyclohexanol | 750 |
| Vanillin | 15 |
| Total | 9700 |

*in dipropyleneglycol
[1)]8,12-Epoxy-13,14,15,16-tetranorlabdane; origin: Firmenich SA, Geneva, Switzerland
[2)]1-(2,6,6-Trimethyl-1,3-cyclohexadien-1-yl)-2-buten-1-one; origin: Firmenich SA, Geneva, Switzerland
[3)]Methyl ionone; origin: Firmenich SA, Geneva, Switzerland
[4)]1-(Octahydro-2,3,8,8-tetramethyl-2-naphtalenyl)-1-ethanone; origin: International Flavors & Fragrances, USA
[5)]3-(4-Tert-butylphenyl)-2-methylpropanal; origin: Givaudan-Roure SA, Vernier, Switzerland
[6)]4/3-(4-Hydroxy-4-methylpentyl)-3-cyclohexene-1-carbaldehyde; origin: International Flavors & Fragrances, USA
[7)]Methyl-cyclopentadecenone; origin: Firmenich SA, Geneva, Switzerland
[8)]Methyl dihydrojasmonate; origin: Firmenich SA, Geneva, Switzerland
[9)](1S,1'R)-[1-(3',3'-Dimethyl-1'-cyclohexyl)ethoxycarbonyl]methyl propanoate; origin: Firmenich SA, Geneva, Switzerland The addition of 300 parts by weight of 1-oxaspiro[2.11]tetradecane to the above-described perfuming composition imparted to the latter a very interesting warm, diffusive, sheer, yet powerful, elegant woody aspect to the fragrance. Said woody aspect was more elegant and better performing than the one conferred by the addition of the same amount of CEDRAMBER® (8-methoxy-2,6,6,8-tetramethyl-tricyclo[5.3.1.0(1,5)] undecane; origin IFF), which accentuate to much the earthy notes of the above described perfuming composition. Moreover, the effect provided by the addition of 1-oxaspiro[2.11]tetradecane was also found to be more balanced than the one conferred by the addition of the same amount of CASHMERAN®.

Example 2

Preparation of a Perfuming Composition

A perfuming composition for a powder detergent was prepared by admixing the following ingredients:

| Ingredient | Parts by weight |
| --- | --- |
| Hexyl acetate | 30 |
| Isobornyl acetate | 275 |
| Benzyldimethylcarbinol acetate | 110 |
| Citronellyl acetate | 25 |
| Styrallyl acetate | 15 |
| Dodecanal | 10 |
| Anisyl acetone | 10 |
| Benzylacetone | 15 |
| Borneol | 15 |
| Citronellol | 200 |
| Verdyl acetate | 100 |
| Verdyl propionate | 100 |
| Dihydromyrcenol | 280 |
| Diphenyloxide | 30 |
| 4-(1,1-Dimethylethyl)-1-cyclohexyl acetate | 25 |
| 50%* GALAXOLIDE ®[1)] | 550 |
| IRALIA ®[2)] | 170 |
| Methylphenylcarbinol | 25 |
| HEDIONE ®[3)] | 35 |
| Nerol | 20 |
| Rose oxide | 15 |
| Cyclohexyl salicylate | 270 |
| Alpha terpineol | 20 |
| Linalool | 85 |
| (E)-4-Methyl-3-decen-5-ol | 30 |
| VERDOX ®[4)] | 70 |
| (2,2-Dimethoxyethyl)benzene | 35 |
| Beta ionone | 100 |
| Total | 2665 |

*in MIP
[1)]1,3,4,6,7,8-hexahydro-4,6,6,7,8,8-hexamethyl-cyclopenta-γ-2-benzopyrane; origin: International Flavors & Fragrances, USA
[2)]Methyl ionone; origin: Firmenich SA, Geneva, Switzerland
[3)]Methyl dihydrojasmonate; origin: Firmenich SA, Geneva, Switzerland
[4)]2-tert-Butyl-1-cyclohexyl acetate; origin: International Flavors & Fragrances, USA The addition of 1100 parts of 1-oxaspiro[2.11]tetradecane to the above-described perfuming composition boosted the woody top-notes of the composition, allowing to obtain excellent performance in the neat application and on wet fabric when compared to ISO E SUPER® (1-(octahydro-2,3,8,8-tetramethyl-2-naphtalenyl)-1-ethanone; origin: International Flavors & Fragrances, USA).

What is claimed is:

1. A method to confer, enhance, improve or modify the odor properties of a perfuming composition or of a perfumed article, which method comprises adding to said composition or article an effective amount of 1-oxaspiro[2.11]tetradecane.

2. A perfuming composition comprising:
   i) as perfuming ingredient, 1-oxaspiro[2.11]tetradecane;
   ii) at least one ingredient selected from the group consisting of a perfumery carrier and a perfumery base; and
   iii) optionally at least one perfumery adjuvant; provided that
   A) a mixture containing 50–60% by weight of ciclotridecanone, about 25–35% of 1-oxaspiro[2.11]tetradecane and 5–10% of cyclodocedacone; and
   B) a mixture consisting of 90–95% of 1-oxaspiro[2.11] tetradecane and 5–10% of cyclodocedacone;

percentage being relative to the total weight of the mixture, are excluded.

3. A perfumed article comprising:
    i) as perfuming ingredient, 1-oxaspiro[2.11]tetradecane; and
    ii) a consumer product base.

4. A perfumed article according to claim 3, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *